United States Patent [19]

Kobayashi

[11] Patent Number: 5,031,654
[45] Date of Patent: Jul. 16, 1991

[54] FLUID PASSAGE VALVE AND MEDICAL INSTRUMENT USING SAME

[75] Inventor: Masahiko Kobayashi, Yamanashi, Japan

[73] Assignee: Terumo Kabushiki Kaisha, Tokyo, Japan

[21] Appl. No.: 547,057

[22] Filed: Jun. 29, 1990

[30] Foreign Application Priority Data

Jul. 4, 1989 [JP] Japan .................................. 1-172713

[51] Int. Cl.⁵ .............................................. A61M 5/40
[52] U.S. Cl. .................... 137/192; 604/127; 604/254
[58] Field of Search ................ 137/192, 399, 533.19; 604/127, 254

[56] References Cited

U.S. PATENT DOCUMENTS 3,503,079  3/1970  Smith ...................... 137/533.19 X
3,965,895  6/1976  Dabney ........................... 604/127
4,131,431 12/1978  Siposs ......................... 604/127 X

FOREIGN PATENT DOCUMENTS 1383975 11/1971 United Kingdom .

Primary Examiner—Alan Cohan
Attorney, Agent, or Firm—Frishauf, Holtz, Goodman & Woodward

[57] ABSTRACT

A fluid passage valve selectively opens and closes a fluid passage port defined in a bottom of a chamber which contains a fluid to be transfused into a patient's vein. The fluid passage valve has a valve member movable toward and away from the fluid passage port to open and close the fluid passage port, and a valve member casing which houses the valve member. The valve member casing has a plurality of limbs which are progressively spread outwardly away from each other in a direction toward the bottom of the chamber, so that the valve member will not be caught by the limbs when the valve member is lowered to close the fluid passage port.

14 Claims, 5 Drawing Sheets

FLUID PASSAGE VALVE AND MEDICAL INSTRUMENT USING SAME

BACKGROUND OF THE INVENTION

The present invention relates to a fluid passage valve and a medical instrument which incorporates such a fluid passage.

Fluid transfusion sets are employed to transfer desired fluids from containers into patient's veins. The fluid transfusion set has a fluid passage valve, which is closed to avoid entry of air into the fluid when the fluid is introduced into a drip infusion tubular member.

One conventional fluid passage valve is shown in FIG. 1 of the accompanying drawings. The fluid passage valve, generally denoted at 2, is combined with a tubular body 6 which defines a constant-rate chamber 4 in a fluid transfusion set. The tubular body 6 has a bottom 8 in which a fluid passage port 10 is defined in the axial direction. The fluid passage port 10 has an open end communicating with the chamber 4 and surrounded by a circular ridge 12. A valve member 14 is separably placed on the ridge 12. The valve member 14 is enclosed by a casing 16 fused to the bottom 8, the casing 16 being of a rectangular vertical cross section. The casing 16 has a large opening or window 18 defined in a side wall 16a which extends perpendicularly to the bottom 8 The tubular body 6 has, on its top cover, a vent passage 20, a fluid inlet passage 22, and a mixture port 24.

When the constant-rate chamber 4 contains a fluid, the valve member 14 floats off the ridge 12 under its own buoyancy, opening the fluid passage port 10 to discharge the fluid from the chamber 4. When the fluid is discharged until its level reaches the bottom 8, the valve member 14 is seated on the ridge 12, closing the fluid passage port 10, so that no subsequent flow of air is permitted through the fluid passage port 10.

When the valve member 14 approaches the fluid passage port 10 as the fluid level is lowered, the edge of the valve member 14 tends to be caught by the side wall 16a of the casing 16. If the valve member 14 gets caught, it does not close the fluid passage port 10 even after the fluid is discharged to the level of the bottom 8, and air flows through the window 18 into the fluid passage port 10. The fluid passage valve 2 incorporated in the fluid transfusion set is therefore disadvantageous in that it allows air and the fluid to be supplied together.

SUMMARY OF THE INVENTION

It is a principal object of the present invention to provide a fluid passage valve which has a casing and a vave member housed in the casing, the casing being constructed to catching the valve member so that the valve member can reliably open and close a fluid passage port, and a medical instrument which incorporates such a fluid passage valve.

Another object of the present invention is to provide a fluid passage valve which is simple in structure and can be mass-produced inexpensively, and a medical instrument which incorporates such a fluid passage valve.

Still another object of the present invention is to provide a fluid passage valve which has a casing and a valve housed in the casing, the casing having an inner surface spreading toward a fluid passage port for thereby preventing the valve member from being caught by the inner surface, and a medical instrument which incorporates such a fluid passage valve.

Yet another object of the present invention is to provide a fluid passage valve for selectively opening and closing a fluid passage port defined in a bottom of a chamber for containing a fluid, the fluid passage valve comprising a valve member movable toward and away from the fluid passage port to open and close the fluid passage port, and a valve member casing which houses the valve member, wherein the valve member casing has a plurality of limbs which are progressively spread outwardly away from each other in a direction toward the bottom of the chamber.

Yet still another object of the present invention is to provide the fluid passage valve further including a top member, the limbs having ends directed toward the bottom of the chamber and curved outwardly away from each other in the direction, and opposite ends converging toward each other and joined by said top member.

A further object of the present invention is to provide the fluid passage valve wherein the limbs are spread substantially linearly in said direction.

A still further object of the present invention is to provide the fluid passage valve further including a top member, the limbs having ends directed toward the bottom of the chamber and curved inwardly toward each other in the direction, and opposite ends converging toward each other and joined by said top member.

A yet further object of the present invention is to provide the fluid passage valve wherein the valve member comprises a thin disc.

A yet still further object of the present invention is to provide a medical instrument including a fluid passage vave as described above.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 1:
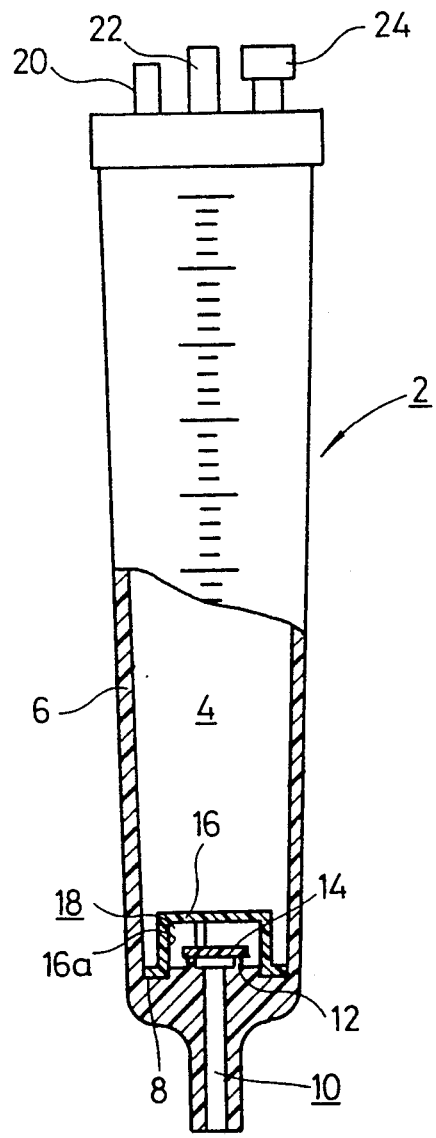
FIG. 1 is a side elevational view, partly in cross section, of a tubular body which defines a constant-rate fluid supply chamber and is combined with a conventional fluid passage valve.
Figure 2:
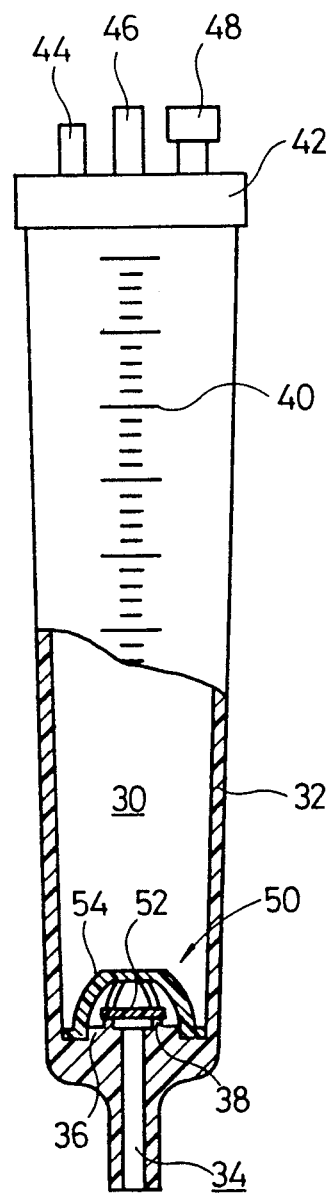
FIG. 2 is a side elevational view, partly in cross section, of a fluid passage valve according to the present invention, which is incorporated in a constant-rate chamber in a fluid transfusion set.

As shown in FIG. 1, a constant-rate chamber 30 in a fluid transfusion set is defined in a tubular body 32 with its diameter progressively smaller downwardly, the tubular body 32 being made of glass, transparent plastic, or the like. The constant-rate chamber 30 has a closed bottom in which a fluid passage port 34 is defined in the axial direction. The fluid passage port 34 has an upper open end surrounded by a circular ridge 38 projecting from a bottom surface 36 of the constant-rate chamber 30. The tubular body 32 has an outer circumferential surface marked with graduations 40 to allow the user to visually check the amount of a fluid contained in the tubular body 32. The top end of the tubular body 32 is closed by a cap 42 in a fluid-tight manner. The cap 42 has a vent passage 44 for introducing ambient air into the constant-rate chamber 30, an inlet passage 46 for introducing a fluid to be transfused into the constant-rate chamber 30, and a mixture port 48 for introducing another fluid which is to be mixed with the fluid introduced from the inlet passage 46.

Figure 3:
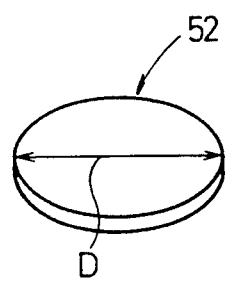
FIG. 3 is a perspective view of a valve member in the fluid passage valve according to the present invention.

A fluid passage valve 50 according to the present invention comprises a valve member 52 which can be seated on and unseated off the ridge 38 to close and open the flow passage port 34, and a valve member casing 54 which houses the valve member 52 and is mounted on the bottom surface 36 in covering relation to the open end of the fluid passage port 34. As shown in FIG. 3, the valve member 52 comprises a very thin, flexible disc-shaped diaphragm having a diameter D. When a fluid such as a drug fluid is introduced into the constant-rate chamber 30, the valve member 52 floats off the ridge 38, thereby opening the fluid passage port 34. When the fluid is discharged from the constant-rate chamber 30, the valve member 52 is lowered and seated on the ridge 38, thereby closing the fluid passage port 34. Preferably, the valve member 52 is made of a synthetic resin such as siicone rubber.

Figure 4:
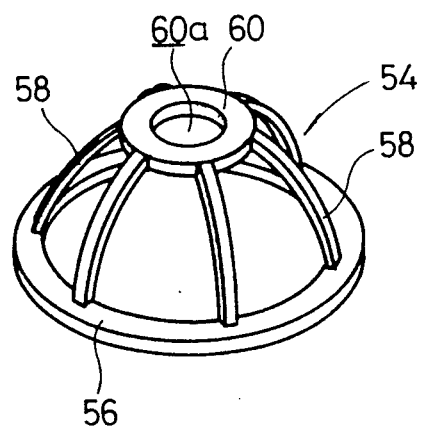
FIG. 4 is a perspective view of a valve member casing of the fluid passage valve according to the present invention.

As shown in FIG. 4, the valve member casing 54 comprises a ring 56 which is fitted in a circular recess defined in the bottom surface 36 of the tubular body 32, a plurality of angularly equally spaced limbs 58 extending obliquely upwardly from the ring 56 and converging toward each other in the upward direction, and a top member 60 joining the distal ends of the limbs 58. In the illustrated embodiment, there are six limbs 58 which are angularly equally spaced by 60°. The top member 60 has a diameter which is greater than 0 but smaller than the diameter D of the valve member 52. The limbs 58 are convex outwardly away from each other as they extend progressively from the top member 60 toward the bottom surface 36. The top member 60 may be of a flat solid surface, but should preferably have a central hole 60a defined therein to allow the fluid to flow smoothly through the valve member casing 54. The bottom of the ring 56 is thermally fused or otherwise joined to the bottom surface 38.

Figure 5:
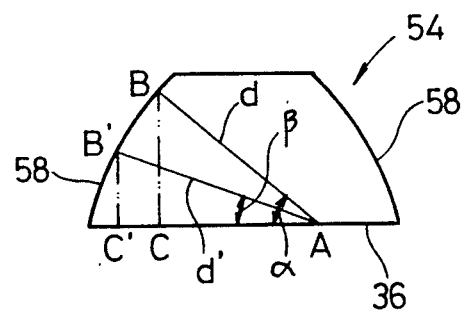
FIG. 5 is a schematic view illustrating the valve member casing shown in FIG. 4.

FIG. 5 schematically shows the valve member casing 54 in its vertical cross section. It is assumed with respect to the valve member casing 54 that straight lines d, d' are drawn from a certain point A on the bottom surface 36 toward one of the limbs 58, the straight line d being inclined at an angle α to the bottom surface 36 and crossing the rib 58 at a point B, and the straight line d' being inclined at an angle β (α > β) and crossing the limb 58 at a point B', and that lines extending from the respectively points B, B' perpendicularly to the bottom surface 36 cross the bottom surface 36 at respective points C, C'. These line segments satisfy the following inequalities:

$$\overline{BC} > \overline{B'C'}$$

$$\overline{AB'} > \overline{AB}$$

It can be seen from the above inequalities that when the valve member 52 floats off the ridge 38 in the fluid introduced in the constant-rate chamber 30 and assumes the position indicated by the line d, and then when the valve 52 approaches the position indicated by the line d' as the level of the fluid is lowered, the valve member 52 is not caught by the inner surface of the limb 58. Therefore, the valve member 52 can reliably open and close the fluid passage port 34.

Figure 6:
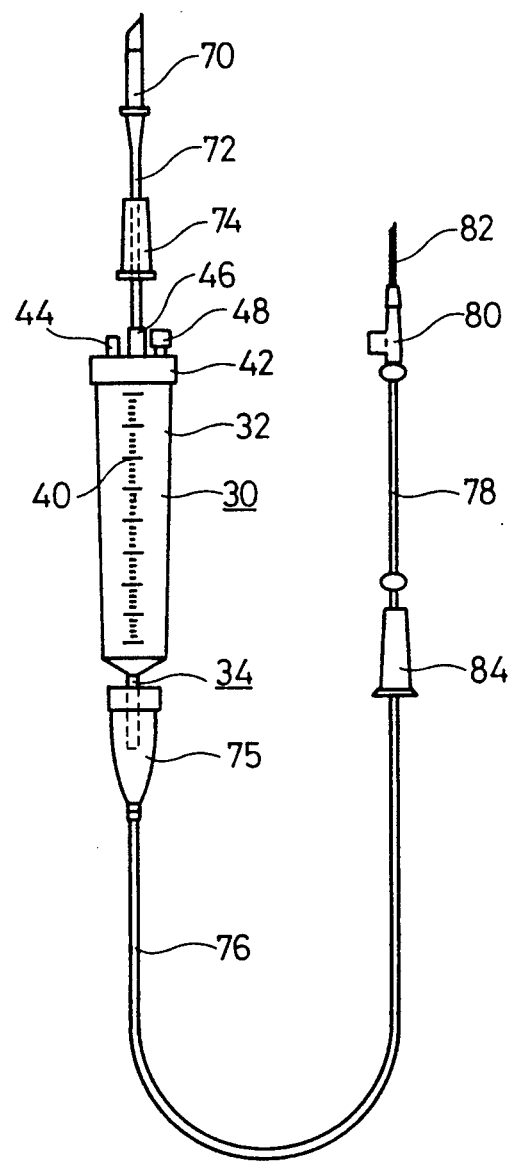
FIG. 6 is a side elevational view of a fluid transfusion set which includes the constant-rate chamber with the fluid passage valve of the invention being incorporated therein.

As shown in FIG. 6, the tubular body 32 with the fluid passage valve 50 combined therein is connected to a fluid transfusion set for use. The fluid transfusion set has a cannula 70 to be inserted into a parenteral fluid container (not shown) and a tube 72 of vinyl chloride which has one end connected to the cannula 70 and the other end joined to the inlet passage 46 of the cap 42 that is fitted over the open end of the tubular body 32 of the constant-rate chamber 30.

The fluid transfusion set also includes a first clamp 74 which can selectively be opened to introduce a fluid from the parenteral fluid container through the cannula 70 and the tube 72 into the constant-rate chamber 30, or closed to cut off the fluid supply from the parenteral fluid container into the constant-rate chamber 30. The amount of the fluid introduced into the constant-rate chamber 30 can accurately be visually checked with the graduations 40 on the outer surface of the tubular body 32. The lower end of the fluid passage port 34 is fused to one end of a drip infusion tubular member 75 of soft transparent vinyl chloride, the other end of which is connected to a tube 76 similar to, but longer than, the tube 72. The tube 76 is connected to a rubber mixture tube 78, an air trap tube 80, and an intravenous cannula 82. The tube 76 has a flow rate adjusting clamp 84 for adjusting the rate of flow of the fluid through the tube 76. The rate of flow of the fluid can be measured through the drip infusion tubular member 75.

The fluid transfusion set which incorporates the fluid passage valve 50 is used as follows: Before use, the flow rate adjusting clamp 84 and the clamp 74 are closed, and then the cannula 70 is inserted into the parenteral fluid container, after which the clamp 74 is opened to introduce about 100 ml of the fluid from the parenteral fluid container into the constant-rate chamber 30. The valve member 52 of the fluid passage valve 50 is unseated off the ridge 38 under its own buoyancy, opening the fluid passage port 34. The fluid in the constant-rate chamber 30 is now allowed to flow through the fluid passage port 34 into the drip infusion tubular member 75. The drip infusion tubular member 75 is slowly compressed with fingers and then released to contain the fluid until the fluid level reaches about half the height of the drip infusion tubular member 75. The clamp 84 is opened to allow the fuid to reach the tip end of the intravenous cannula 82, and thereafter the clamp 84 is closed. The clamp 74 is kept open until the fluid is contained in the constant-rate chamber 30 in an amount to be transfused, after which the clamp 74 is closed. The fluid transfusion set is now ready for fluid transfusion.

Then, the intravenous cannula 82 is inserted into a vein of a patient, and the flow rate adjusting clamp 84 is gradually loosened to transfer the fluid into the patient. During the transfusion, the rate at which the fluid is transfused can be adjusted by the clamp 84 while the rate is being observed through the drip infusion tubular member 75.

As the fluid contained in the constant-rate chamber 30 is reduced in quantity, the valve member 52 is lowered. Since the valve member casing 54 is constructed not to catch the valve member 52, as described above, the valve member 52 is not caught by the inner surfaces of the limbs 58, but can reliably be seated on the ridge 38 to close the fluid passage port 34. After the fluid passage port 34 is closed by the valve member 52, the fluid or air is blocked thereby, and the fluid transfusion is brought to an end.

Figure 7:
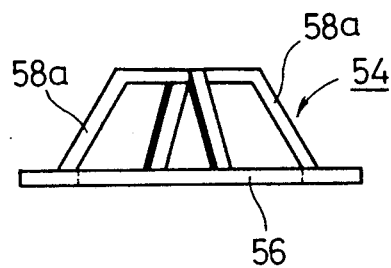
FIG. 7 is a side elevational view of a valve member casing according to another embodiment of the present invention.

FIG. 7 shows a valve member casing 54 according to another embodiment of the present invention. The valve member casing 54 shown in FIG. 7 differs from the valve member casing shown in FIGS. 2 through 6 in that limbs 58a are spread linearly from the top member toward the ring 56. The other structural details of the valve member casing 54 shown in FIG. 7 are the same as those of the valve member casing shown in FIGS. 2 through 6, and will not be described in detail.

Figure 8:
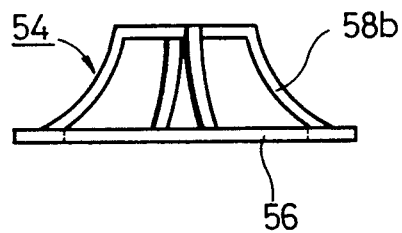
FIG. 8 is a side elevational view of a valve member casing according to still another embodiment of the present invention.

FIG. 8 illustrates a valve member casing 54 according to still another embodiment of the present invention. The valve member casing 54 shown in FIG. 8 differs from the valve member casing shown in FIGS. 2 through 6 in that limbs 58b are convex inwardly toward each other as they extend from the top member toward the ring 56.

With the present invention, as described above, when the level of the fluid contained in the constant-rate chamber is lowered as the fluid is discharged, the valve member is also lowered. While the valve member is being lowered, the valve member is not caught by the limbs of the valve member casing since the ribs are progressively spread outwardly toward the bottom surface of the constant-rate chamber. Therefore, the valve member can reliably close the fluid passage port when the fluid is fully discharged from the constant-rate chamber. When the level of the fluid in the constant-rate chamber is increased, the valve member is lifted away from the open end of the fluid passage port. Accordingly, the fluid passage port can reliably be opened and closed by the valve member. At the time no fluid is contained in the constant-rate chamber, the fluid passage port is reliably closed by the valve member, so that air or the like is prevented from being mixed into the fluid through the air passage port.

Although certain preferred embodiments have been shown and described, it should be understood that many changes and modifications may be made therein without departing from the scope of the appended claims.

What is claimed is:

1. A fluid passage valve for selectively opening and closing a fluid passage port formed in the bottom of a chamber, comprising:
   a disc type valve member moveable toward and away from said fluid passage port to open and close said fluid passage port;
   a valve member casing for housing said disc type valve member, said valve member casing having:
   a top portion;
   a bottom portion having a first aperture therethrough, said bottom portion being larger than said top portion, and said bottom portion being mounted on said bottom of said chamber so that said first aperture surrounds said fluid passage port; and
   a plurality of spaced apart limbs connecting said top and bottom portions;
   the distance between adjacent ones of said limbs being smallest at said top portion, and increasing continuously in the direction away from said top portion toward said bottom portion such that said distance between said adjacent ones of said limbs is largest at said bottom portion.

2. A valve according to claim 1 wherein each of said limbs is bowed outwardly radially away from said fluid passage port.

3. A valve according to claim 1 wherein each of said limbs is bowed inwardly toward said fluid passage port.

4. A valve according to claim 1 wherein said limbs are linear.

5. A valve according to claim 1 wherein said bottom portion includes a first member which has said first aperture formed therethrough.

6. A valve according to claim 5 wherein said limbs are attached to said first member and to said top portion.

7. A valve according to claim 1 wherein said top portion includes a second member having a second aperture therethrough and wherein said limbs are attached to said second member.

8. A medical instrument comprising:
   a chamber having a bottom;
   a fluid passage port formed in said bottom of said chamber; and
   a fluid passage valve for selectively opening and closing said fluid passage port;
   said fluid passage valve including:
   a disc type valve member moveable toward and away from said fluid passage port to open and close said fluid passage port; and
   a valve member casing for housing said valve member;
   said valve member casing having:
   a top portion;
   a bottom portion having a first aperture therethrough, said bottom portion being larger than said top portion, and said bottom portion being mounted on said bottom of said chamber to surround said fluid passage port; and
   a plurality of spaced apart limbs connecting said top and bottom portions;
   the distance between adjacent ones of said limbs being smallest at said top portion, and increasing continuously in the direction away from said top portion toward said bottom portion such that said distance between said adjacent ones of said limbs is largest at said bottom portion.

9. A medical instrument according to claim 8 wherein each of said limbs is bowed outwardly radially away from said fluid passage port.

10. A medical instrument according to claim 8 wherein each of said limbs is bowed inwardly toward said fluid passage port.

11. A medical instrument according to claim 8 wherein said limbs are linear members.

12. A medical instrument according to claim 8 wherein said bottom portion includes a first member, said first aperture being formed in said first member.

13. A medical instrument according to claim 12 wherein said limbs are attached to said first member and to said top portion.

14. A medical instrument according to claim 8 wherein said top portion includes a second member having a second aperture formed therethrough and wherein said limbs are attached to said second member.

* * * * *